(12) United States Patent
Busch et al.

(10) Patent No.: US 9,241,882 B2
(45) Date of Patent: *Jan. 26, 2016

(54) AGENT FOR PROTECTION OF TOOTH SURFACES, IN CONJUNCTION WITH CONVENTIONAL BLEACHING METHODS, BY BIOMIMETIC DEPOSITION OF FLUORAPATITE

(75) Inventors: Susanne Busch, Neu Anspach (DE); Andreas Utterodt, Neu Anspach (DE); Marcus Hoffmann, Usingen (DE); Christoph Maetzig, Alzenau (DE)

(73) Assignee: HERAEUS KULZER GMBH, Hanau (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/444,224

(22) Filed: Apr. 11, 2012

(65) Prior Publication Data

US 2012/0195941 A1 Aug. 2, 2012

Related U.S. Application Data

(62) Division of application No. 11/942,090, filed on Nov. 19, 2007, now abandoned.

(30) Foreign Application Priority Data

Nov. 21, 2006 (DE) .......................... 10 2006 055 223

(51) Int. Cl.

| | | |
|---|---|---|
| A61Q 11/00 | (2006.01) | |
| A61K 6/033 | (2006.01) | |
| A61K 8/24 | (2006.01) | |
| A61K 8/21 | (2006.01) | |
| A61K 8/02 | (2006.01) | |
| A61K 8/04 | (2006.01) | |
| A61K 8/19 | (2006.01) | |
| A61K 8/65 | (2006.01) | |

(52) U.S. Cl.
CPC ................ *A61K 8/24* (2013.01); *A61K 8/0208* (2013.01); *A61K 8/042* (2013.01); *A61K 8/19* (2013.01); *A61K 8/65* (2013.01); *A61Q 11/00* (2013.01); *A61K 2800/88* (2013.01)

(58) Field of Classification Search
USPC ........ 424/601, 602, 52, 49, 57, 492; 433/215, 433/216, 217.1

See application file for complete search history.

(56) References Cited

U.S. PATENT DOCUMENTS

| 4,083,955 A | 4/1978 | Grabenstetter et al. |
|---|---|---|
| 4,397,837 A * | 8/1983 | Raaf et al. ........................ 424/51 |
| 5,603,922 A | 2/1997 | Winston et al. |
| 5,851,514 A | 12/1998 | Hassan et al. |
| 5,858,333 A | 1/1999 | Winston et al. |
| 6,102,050 A | 8/2000 | Marcon |
| 6,303,104 B1 | 10/2001 | Winston et al. |
| 6,419,905 B1 | 7/2002 | Hernandez |
| 6,521,251 B2 | 2/2003 | Askill et al. |
| 2002/0028251 A1 * | 3/2002 | Okay ............................ 424/498 |
| 2002/0187181 A1 | 12/2002 | Godbey et al. |
| 2003/0219388 A1 * | 11/2003 | Kropf et al. ...................... 424/50 |
| 2005/0220724 A1 | 10/2005 | Busch et al. |
| 2005/0281759 A1 | 12/2005 | Tung |
| 2006/0110340 A1 | 5/2006 | Tung |
| 2007/0218017 A1 | 9/2007 | Busch et al. |

FOREIGN PATENT DOCUMENTS

| AT | 372272 B | 9/1983 |
|---|---|---|
| DE | 33 03 937 A1 | 6/1984 |
| DE | 100 63 945 A1 | 7/2002 |
| DE | 102 23 157 C1 | 10/2003 |
| DE | 10 2004 054 584 A1 | 5/2006 |
| EP | 0 845 976 B1 | 3/2004 |
| EP | 1 645 263 A1 | 4/2006 |
| FR | 2170018 A | 9/1973 |
| JP | 06 024929 A | 2/1994 |
| JP | 2000 051804 A | 2/2000 |
| JP | 2002 293725 A | 10/2002 |
| WO | 98 10736 A | 3/1998 |
| WO | 01 01930 A2 | 1/2001 |
| WO | 2005 027863 A1 | 3/2005 |
| WO | 2005 092271 A | 10/2005 |
| WO | 2006050966 A | 5/2006 |
| WO | 2007 066837 A | 6/2007 |

OTHER PUBLICATIONS

Bitter et al; "The effect of four bleaching agents on the enamel surface; A scanning electron microscopic study": Dental Research; Quintessence International, vol. 24, No. 11, 1993; pp. 817-824.

Attin et al; "Susceptibility of enamel surface to demineralization after application of fluoridated carbamide peroxide gels"; Caries Research; 2003, 37; pp. 93-99.

(Continued)

*Primary Examiner* — Lezah Roberts
(74) *Attorney, Agent, or Firm* — Norris McLaughlin & Marcus, P.A.

(57) ABSTRACT

An agent for protection of tooth surfaces, in conjunction with conventional bleaching methods, by biomimetic deposition of fluorapatite, containing A at least one preformulated 50-1000 µm thick gel film A, containing A1 at least one gel former, A2 water or a mixture of water and an organic solvent, A3 phosphate or hydrogen phosphate ions, A4 optionally fluoride, A5 optionally at least one amino acid, A6 optionally one carboxylic acid or a buffer system for a pH value from 4 to 7.

B at least one 50 µm to 5 mm thick gel film B, containing

B1 at least one gel former,

B2 water,

B3 calcium ions $Ca^{2+}$.

8 Claims, 1 Drawing Sheet

(56) References Cited

OTHER PUBLICATIONS

Cavalli et al; "Effect of carbamide peroxide bleaching agents on tensile strength of human enamel"; Dental Materials; 2004; 20; pp. 733-739; Elsevier.

Nathanson, et al; "Bleaching vital teeth: a review and clinical study": Compend Contin Educ Dent., vol. VIII, No. 7; pp. 490-498.

Nathanson; "Vital tooth bleaching: Sensitivity and pulpal considerations"; JADA, vol. 128, Apr. 1997; pp. 41S-44S.

* cited by examiner

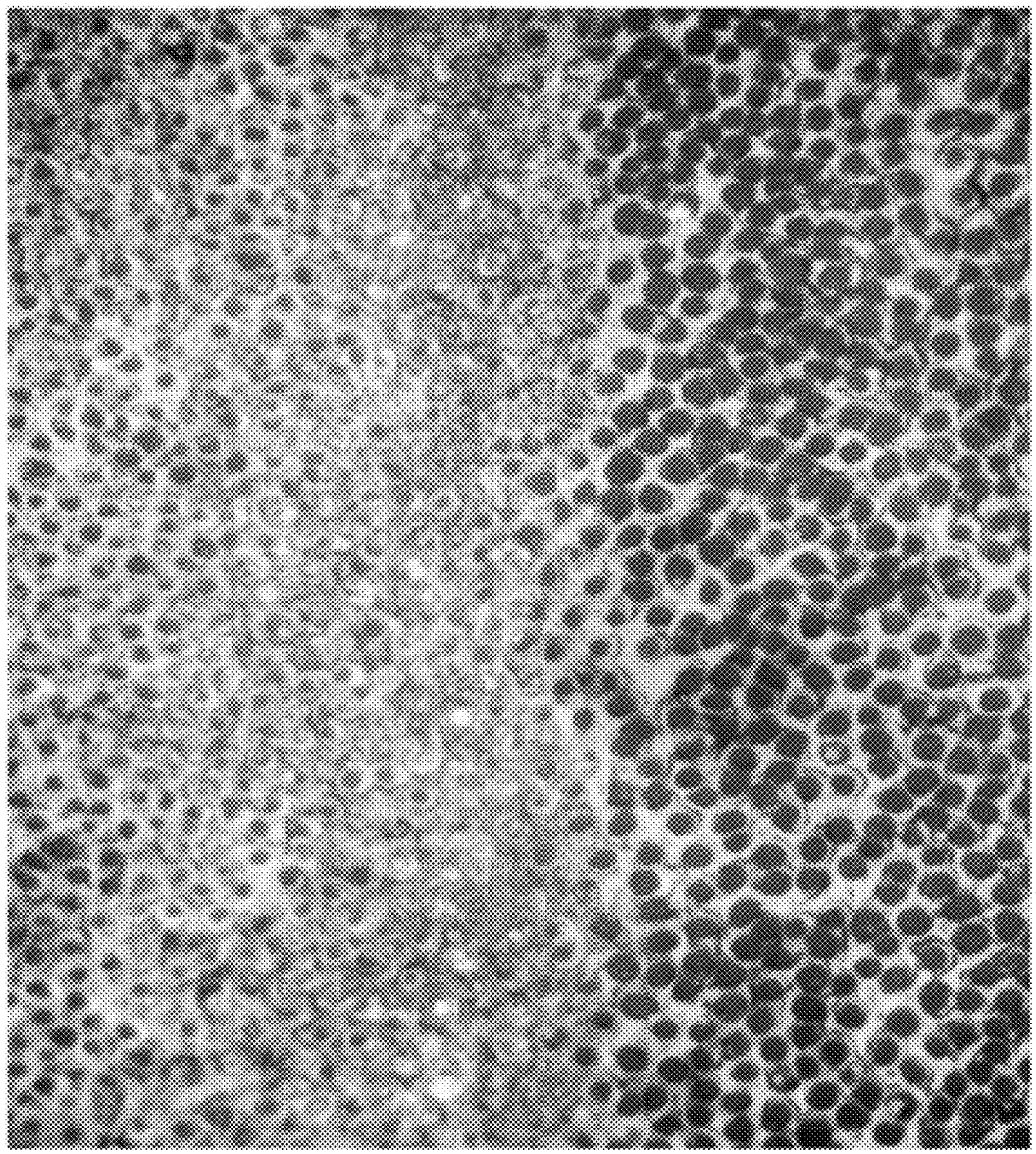

AGENT FOR PROTECTION OF TOOTH SURFACES, IN CONJUNCTION WITH CONVENTIONAL BLEACHING METHODS, BY BIOMIMETIC DEPOSITION OF FLUORAPATITE

This application is a division and claims priority of U.S. patent application Ser. No. 11/942,090, filed Nov. 19, 2007, now pending, which, in turn, claims priority of German Patent Application No. 10 2006 055 223.7, filed Nov. 21, 2006, the entire contents of which applications are incorporated herein by reference.

The invention concerns an agent to protect dental surfaces, in conjunction with conventional bleaching methods, by biomimetic deposition of fluorapatite.

BACKGROUND

Bleaching systems that act by means of strong oxidizers are mostly used for brightening of teeth. Depending on the form of application, the concentrations lie between 10-35% peroxide. In particular, concentrated hydrogen peroxide solutions or carbamide peroxide are used. The action mechanism is based on oxidative decoloration of incorporated colorants. They have an aggressive effect on the oral mucosa, so the contact must absolutely be avoided. However, strong oxidizers also degrade structure-relevant proteins in the enamel. The content of natural macromolecules in dental enamel depends on the degree of maturation and is about 1-2 wt. % in adults. Proteins are preferably found on the surface of enamel prismatic units, but can also be integrated in the crystal structure. Composite systems of an inorganic mineral and organic components (preferably proteins and polysaccharides) are characteristics of biomineralization. The specific interaction leads to increased rupture strength. If the organic components are chemically removed, embrittlement must be reckoned with. Accessibility for contaminants, at least in the first days after treatment, is also increased during oxidative tooth brightening, and the sensitivity to pain is sometimes strongly increased. A fine pore system presumably becomes passable by oxidation of the biological matrix, which was previously filled by protein. Because of this, pain stimuli can be conducted more readily to the tooth nerve and undesired foreign substances can diffuse in better. This would explain why bleaching applications must often be repeated and treated teeth can be vulnerable to inflammation. Many bleaching systems function at low pH values, which can also lead to demineralization and entail additional weakening for the tooth. Topographic investigations on bleached human teeth show a detectable increase in natural porosity (cf. Bitter N. C. and Sanders J., L.: *The effect of four bleaching agents on the enamel surface: A scanning electron microscopic study. Quintessence Int* 1993, 24: 817-24). In addition, increased sensitivity to acid attack results. Although the hardness of the tooth shows no measurable reduction after the bleaching procedure, studies on bleached teeth demonstrate a distinct reduction in microhardness and intensified dissolution phenomena after simulated demineralization-remineralization cycles. The effect is somewhat reduced by providing fluoride, but weakening is not eliminated (cf. Attin T., Kocabiyik M., Buchalla W., Hanning C., Becker K.: *Susceptibility of Enamel Surfaces to Demineralization after Application of Fluoridated Carbamide Peroxide Gels*, Caries Res 2003: 37: 93-99). Another study demonstrates that the tensile strength and rupture strength of enamel diminishes by up to 30% after exposure to bleaching solutions (see: Cavalli, V. et al.: *Effect of carbamide peroxide bleaching agents on tensile strength of human enamel*. Dental Materials (2004) 20, 733-9). A pain study demonstrates that after treatment with 35% hydrogen peroxide solution, ⅔ of the patients reported moderate to severe pain, which lasted up to 48 hours after treatment (see Nathanson D., Parra C.: *Bleaching vital teeth: A review and clinical study*. Compend. Contin. Educ. Dent. 1987; 8(7): 490-7). The studies provide no clear indication of irreversible pulp damage, but in animal experiments, cases of massive inflammation, dentin resorption up to death of the pulp occurred after bleaching of vital dog teeth (see Nathanson, D.: *Vital tooth bleaching: Sensitivity and Pulpal considerations*, JADA, 128 (April 1997) 41-4). A prerequisite for conventional bleaching procedures, in each case, are healthy teeth. If hypersensitive teeth, exposed tooth necks or caries are present, bleaching can irreversibly damage the tooth nerve. It is also conceivable that damage from repeated bleaching can accumulate in healthy teeth.

In order to counteract the problem, attempts are made to fill exposed micropores by biomimetic remineralization, and also to apply an apatite protective layer. Since apatite, and especially fluorapatite, from pH 5 represents the thermodynamically most stable calcium phosphate, it can be easily demonstrated that, at physiological pH value, apatite is preferably formed in the presence of calcium and phosphate ions. To correspond to the composite nature of the biological model, mineralization occurs in the presence of an organic gel. This means that macromolecules are integrated in the apatite structure.

RELATED ART

Some methods are described in the patent literature, whose objective is to balance the effect of bleaching that weakens the tooth substrate by remineralization. Calcium- and phosphate-containing salts are either added to the oxidizer or the bleaching agent itself represents a calcium- and/or phosphate-containing peroxide. U.S. Pat. No. 6,521,251 describes a composition that contains calcium phosphates, in addition to carbamide, the solubility of which is somewhat better than that of apatite, like mono-, di- or tricalcium phosphate. However, all these calcium phosphates are only slightly water-soluble and, for this reason, a more abrasive effect than a remineralizing one is expected. U.S. Pat. No. 5,851,514 actually describes, among other things, the addition of dicalcium phosphate as an abrasive. U.S. Pat. No. 6,419,905 mentions the addition of potassium salts (for example, phosphates) and fluoride to peroxide. Fluoride is suitable for bonding calcium and phosphate ions from saliva, so that fluorapatite precipitates. If additional ions are not added, formation of $CaF_2$ is also observed. The calcium fluoride particles can be stored in the plaque and release fluoride over a longer period, since they are somewhat more soluble than apatite. However, all teeth are freed of plaque by intensive cleaning before professional bleaching. JP 20000051804 describes parallel use of concentrated phosphoric acid, concentrated $H_2O_2$ and fluorapatite powder. A problem appears here with the use of concentrated phosphoric acid, which can noticeably dissolve healthy dental enamel. In addition, the bleaching solution has a strong etching effect and must not come in contact with the gums, which, however, applies, to a somewhat lesser degree, for all tooth brighteners that have an oxidative effect. In addition, repeated application does not lead to an increase in the remineralization layer. It is suspected that the dental enamel dissolved here, at best, is reprecipitated. An acid-free application is described in U.S. 20050281759. Calcium peroxophosphate is proposed as an essential ingredient. This idea has the advantage that a single substance is supposed to have a brightening and remineralizing effect, since release of calcium and phosphate ions is triggered parallel with oxidation. It is not clear whether the salts can contribute to noticeable buildup over the relatively short exposure time. U.S. Pat. No. 6,303,104 describes a two-component system, free of oxidizer, from soluble calcium and phosphate salts, which is also supposed to have a brightening effect. Brightening is supposed to be produced by the additional sodium gluconate, which complexes coloring metal ions (for example, iron) from dental enamel. During mixing of the components, precipitation of the poorly soluble calcium phosphates must immediately be reckoned with and it cannot be recognized why pronounced remineralization should occur, especially since the product is a toothpaste that remains in contact with the tooth surfaces for only a few minutes. The decoloring effect is also reduced to complexable metal ions and presumably will only exhibit an effect in the outermost enamel layers. U.S. Pat. No. 6,102,050 describes a dental floss with titanium dioxide particles that is attributed a brightening, remineralizing and desensitizing effect on the interproximal surfaces. Here, titanium dioxide microparticles with a size of 0.1-1.5 µm are supposed to act both as a mild abrasive and are absorbed by the enamel, which is connected with a brightening effect. Presumably, the particles, at best, can be mechanically incorporated in appropriate cavities, which does not promise stable anchoring. All patents described thus far do not consider that biominerals only reach their high structural organization and stability because they are formed in the presence of special biomolecules that dictate micro- and macrostructuring. WO 2005/027863 describes a dental hygiene agent, which is supposed to have a cleaning, remineralizing, desensitizing and brightening effect. A nanoscale apatite is mentioned as an active component for remineralization and brightening, which is precipitated in the presence of an aqueous gelatin solution and therefore has incorporated polypeptides. It is attributed to this material that it forms a protective film of dentin-like structure by so-called "neomineralization" on the tooth surface, which causes surface smoothing and can close open dentin tubuli. This effect is astonishing, since only 0.01-2 wt. % "nanites" (WO 01/01930) are preferably contained in the dental hygiene agent. The exposure to the active substances is only a few minutes daily. A pronounced mineral deposition therefore cannot be considered. Nanoscale particles are also colorless, so that incorporation of nanite should not lead to a color change. A continuous growth of film thickness during longer application of the agent is not observed. In addition, dentin is not suitable for protecting the teeth from corrosive attack.

The possibility of a continuously growing FAP-layer with an enamel- or dentin-like structure is offered by the technique described in U.S. 20005220724 and DE 1020040545847. Water-soluble phosphate and fluoride salts are incorporated in buffered gel A, calcium ions in gel B. Optionally separated by an ion-free protective layer, the gelatin-glycerol gels, solid at physiological temperature, are applied in succession to the tooth surfaces during heating. Depending on the exchange cycles of the gels, an increase in layer thickness can be observed. The growth rates amount to a maximum of 3-5 µm/day. The biological structures of the tooth material are formed individually by fluorapatite, but cavities through open dentin tubuli are closed after a few exchange cycles. With respect to human application, it turns out to be unfavorable that the gels must be heated before application. By application of the second and third gel layer, underlying already applied gel layers can be reliquefied and intermingle undesirably with the overlying layers. In particular, smaller forms of administration quickly dry up on exposure to air and liquefaction by heating is then no longer possible without a problem. The method does not permit application of precisely defined amounts of gel to the tooth. In addition, the three gel layers, up to 6 mm thick, spread strongly, which leads to problems in protective systems, like braces or bandages, since space must be created here for large gel reservoirs.

STATEMENT OF THE TASK

The objective is to achieve tooth protection or regeneration of smaller tooth defects, especially during final treatment of oxidatively brightened teeth.

SUMMARY OF THE INVENTION

Methods and agents are described that can be used for deliberate biomimetic mineralization of apatite on tooth surfaces, as a procedure following oxidative tooth brightening, with the objective of tooth protection. It is expected that this reparative final treatment compensates for the loss of minerals and proteins resulting from the bleaching process and the increased brittleness from direct buildup of a composite from a bioorganic gel, and entails extension of the bleaching effect. As a result of the long action time of the active minerals, highly ordered crystalline layers, intergrown with the substrate, can effectively form. The pores and cracks formed by oxidative attack are closed by remineralization, so that renewed decoloration is reduced. If the protective layer is abraded with time, accumulation of new discoloration in the outer dental enamel layers is ruled out. Protective treatment of brightened teeth is connected with the agent according to the invention with the objective of reducing or eliminating undesired side effects of bleaching and improving the stability of the teeth. The tendency toward decoloration of brightened teeth can be reduced. It can be expected that the tooth not only acquires its original stability again more quickly, but that the initially increased sensitivity declines much more quickly and the brightening effect from the protective layer lasts longer. Because of the shortened diffusion paths of the ions connected with the limited layer thickness, back-mixing of phosphate with calcium salts is reduced and special favoring of the direct tooth surface as a heterogeneous nucleation surface remains even without retaining the ion-free protective gel in pronounced fashion. Because of the defined layer thickness, reproducibly identical gel amounts can be applied to the tooth. The layer can be polished with SiC grinding paper.

DETAILED DESCRIPTION OF THE INVENTION

The invention concerns agents for protection of tooth surfaces after conventional bleaching methods by biomimetic deposition of fluorapatite, having A at least one preformulated 50-1000 µm thick gel film A, containing a gel former,
  water or a mixture of water and an organic solvent
  0.01-2 mol per liter of gel phosphate or hydrogen phosphate,
  optionally fluoride,
  optionally at least one amino acid,
  optionally one carboxylic acid or a buffer system for a pH value from 4 to 7,
B at least one 50 µm to 5 mm thick gel film B, containing a gel former,
  water,
  0.05 to 3 mol/L calcium ions $Ca^{2+}$.

Use of such thin, preformulated gel films compensates for the drawbacks described from U.S. 20005220724, which result from the use of gels applied warm. The thickness of gel A is preferably 150-500 μm. The concentration of phosphate salts is preferably 0.08 to 0.3 mol. The thickness of gel B is preferably 200 to 600 μm. The concentration of gel B is preferably 0.13 to 1 mol/L.

Phosphoric acid or its alkali salts are preferably considered as phosphate or hydrogen phosphate source. It was surprisingly found that by using the thin gel layers, higher ion concentrations can be accommodated in the gel, without threatening preference of the tooth surface as location of heterogeneous nucleation. In order to store higher concentrations of calcium and phosphate ions in soluble form in the gel, amino acids are preferably added to the gelatin. The amino acids act, because of their bonding interaction with the mineral salts, as a depot and optimize their availability. It is assumed that during local depletion of calcium and phosphate as a result of mineralization, the amino acids release ions by shifting the equilibrium. In principle, all amino acids are suitable for bonding calcium and phosphate ions, since, as an amphoteric molecule, each amino acid has both an acid and a basic side group. The optimal effectiveness is strongly pH-dependent. In the direct vicinity of the mineralization front, as a result of the acid-liberating apatite formation, especially those amino acids are active that have acid groups and release calcium. The availability of phosphate in gel A can preferably be increased by adding amino acids with additional basic groups. To increase the solubility, all substances that have bonding sites for calcium and phosphate ions are also suitable, without precipitating them or having a toxic effect on the human body. These include vitamins (for example, ascorbic acid), oligopeptides, carboxylic acids, and especially fruit acids, like malic acid, citric acid or pyruvic acid, or sequestering agents, like EDTA. This list is inclusive, but not exclusive. In order to keep the pH value constant during mineralization, acetic acid can be used. All physiologically compatible buffer systems that have their maximum effectiveness in the corresponding buffer range between 4 and 7 are also suitable. Dicarboxylic acids, like succinic acid, malonic acid, or amino acids, like glutamic acid, would be suitable. This list is inclusive, but not exclusive.

DE 1020040545847 describes that pre-wetting of the teeth with 0.05-1 N NaOH has an effect on morphology and growth rate of the layers. It is expected that even slight deviations in this procedure will lead to different wetting with alkali and significantly influence the result.

A method is described here, in which small amounts of gelatin are added to an alkali, preferably 1-15 wt. %, especially 5-10 wt. %, which is blown after a defined exposure time with defined pressure. Very thin films are reproducibly formed on the tooth surface on this account, through which the initial mineralization is particularly favored. Pretreatment can be conducted according to the invention, both with a liquid, a viscous gel or a solidified gel, which is heated before application.

BRIEF DESCRIPTION OF THE DRAWING

The invention will now be described in greater detail with reference to the drawing, wherein:

FIG. 1 depicts a light microscope image of a tooth disk, whose left half was subjected to two gel treatment cycles; the right half was covered.

EXAMPLE

A 2 mm-thick disk, containing a dentin and an enamel area, was sawn out from molars. All tooth samples were polished and treated per molar for 10 seconds with 25% phosphoric acid, in order to expose the dentin tubuli and make the native enamel structure visible. The samples were then washed intensely under running water. The teeth were treated 4× each for 8 minutes with 35% hydrogen peroxide gel, and then rinsed with water and subjected to color measurement. A tooth in the enamel area shows distinct crack formation related to oxidation treatment. A 1 N NaOH solution, saturated with calcium hydroxide, was mixed with 5 wt. % gelatin for alkaline pretreatment. The tooth disks were coated with the solution, and then the moisture uniformly blown. For the phosphate ion-containing gel, a solution was prepared, containing 0.6 mol/L $Na_2HPO_4$, 0.1 mol/L NaF, 0.3 mol/L asparagine and 330 mL 2 N/L acetic acid. 16 mL of the solution was processed with 6 g glycerol and 10 g of a 300 bloom pork rind gelatin during heating to a viscous gel. By means of a doctor blade, 300 μm thick gel films were applied from the still liquid gel, dried and then cut into matching pieces. A 1 M calcium chloride solution was used for the calcium gel. Further processing corresponds to that of the phosphate gel.

The tooth disks were now covered with a piece of phosphate gel and a piece of calcium gel. In order to make the morphological change of the tooth surface distinct, a disk was half-covered with parafilm beforehand, so that only half could remineralize. The samples were stored in a climate-controlled cabinet at 37° C. and 95% humidity, washed daily and subjected to renewed gel treatment. FIG. 1 shows a light microscope image of the half-covered tooth disk after the fourth exchange. The dentin tubuli are fully closed and traces of polishing could no longer be seen.

Faults in the enamel are also grown over. After a 5-fold gel exchange, the samples were cleaned and placed in coffee for 40 hours. They were then cleaned with a brush under running water. The bleached sample shows a distinctly darker discoloration than the coated sample. To permit a comparison, an untreated sample was measured by colorimetry before and after staining in coffee.

In order to quantify the color change, the samples were measured versus white before and after staining with a 2-channel spectrophotometer for color and reflection measurement Spectraflash 600 Plus with the CIE L*a*b System with the diaphragm 3 mm X4SAV. Staining in all samples leads to darkening and a change in color tone in the direction yellow and red. Table 1 shows the delta-values before and after staining of the dentin for the bleached tooth (sample 1), the bleached and coated tooth (sample 2) and the exclusively stained sample (sample 3). The results clearly show that the bleached sample is decolored more strongly than the untreated sample and much more strongly than the coated sample. This means the coated tooth disk shows weaker decoloration, both relative to the bleached and untreated samples.

TABLE 1

|  | ΔE | ΔL* | Δa* | Δb* | ΔC* | Δh |
| --- | --- | --- | --- | --- | --- | --- |
| Sample 1 | 23.34 | −17.01 | 7.69 | 14.01 | 15.58 | −3.53 |
| Sample 2 | 5.71 | −2.53 | 4.84 | −1.66 | −0.78 | −5.06 |
| Sample 3 | 16.12 | −6.74 | 9.75 | 10.93 | 12.35 | −7.86 |

FIG. 1 shows the structure change from gel treatment. It is apparent as a leveling of the surface.

What is claimed is:

1. A method for protecting a tooth surface, after tooth bleaching methods, by biomimetic deposition of apatite or fluorapatite on the tooth surface, comprising the following steps:
   (a) providing at least one gel film A and at least one gel film B;
   (b) applying said at least one gel film A to the tooth surface; and subsequently
   (c) covering the at least one gel film A with the at least one gel film B; and
   (d) repeating steps (a)-(c) as necessary for a period of time sufficient to achieve biomimetric deposition of apatite or fluorapatite on the tooth surface;
   wherein:
   said at least one gel film A is 50-1000 μm thick and comprises:
      A1 at least one gel former,
      A2 water or a mixture of water and an organic solvent,
      A3 phosphate or hydrogen phosphate ions,
      A4 optionally fluoride,
      A5 optionally at least one amino acid, and
      A6 optionally one carboxylic acid or a buffer system for a pH value from 4 to 7; and
   said at least one gel film B is 50 μm to 5 mm thick and comprises:
      B1 at least one gel former,
      B2 water, and
      B3 calcium ions $Ca^{2+}$.

2. Method according to claim 1, in which the at least one gel film A comprises:
   A3 0.01-2 mol per liter of gel of a phosphate or hydrogen phosphate.

3. Method according to claim 1, in which the at least one gel film B comprises:
   B3 0.05 to 3 mol per liter of gel calcium ions $Ca^{2+}$.

4. Method according to claim 1, in which the gel former is gelatin.

5. Method according to claim 4, in which the gelatin concentration in A and B is 1-15 wt. % each.

6. Method according to claim 5, in which the gelatin concentration is 5-10 wt. %.

7. Method according to claim 1, in which the phosphate or hydrogen phosphate is present as dissociated $Na_2HPO_4$, $(NH_4)_2HPO_4$ or $K_2HPO_4$.

8. Method according to claim 1, in which the calcium ions are present as dissociated $CaCl_2$.

* * * * *

UNITED STATES PATENT AND TRADEMARK OFFICE
CERTIFICATE OF CORRECTION

PATENT NO. : 9,241,882 B2
APPLICATION NO. : 13/444224
DATED : January 26, 2016
INVENTOR(S) : Busch et al.

It is certified that error appears in the above-identified patent and that said Letters Patent is hereby corrected as shown below:

In the claims,

Column 7, line 12, "biomimetric" -- should read -- biomimetic --.

Signed and Sealed this
Ninth Day of August, 2016

Michelle K. Lee
*Director of the United States Patent and Trademark Office*